United States Patent
Cavallaro

(10) Patent No.: US 7,150,200 B1
(45) Date of Patent: Dec. 19, 2006

(54) MINIATURE AXISYMMETRIC STREAMLINE TENSILE (MAST) SPECIMEN

(75) Inventor: Paul V. Cavallaro, Raynham, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 78 days.

(21) Appl. No.: 10/814,360

(22) Filed: Apr. 1, 2004

(51) Int. Cl.
*G01N 3/08* (2006.01)
*G01N 3/02* (2006.01)

(52) U.S. Cl. .......................... 73/826; 73/856
(58) Field of Classification Search ................ 73/826, 73/856
See application file for complete search history.

(56) References Cited

U.S. PATENT DOCUMENTS 5,286,108 A * 2/1994 Whatley et al. ............ 374/49

6,460,418 B1 * 10/2002 Hiyoshi ..................... 73/800

OTHER PUBLICATIONS

Donald W. Oplinger et al, On the Streamline Specimen for Tension Testing of Composite Materials,Paper, 1985,pp. 532-555,American Society for Testing and Materials, Philadelphia.

* cited by examiner

*Primary Examiner*—Max Noori
(74) *Attorney, Agent, or Firm*—James M. Kasischke; Jean-Paul A. Nasser; Michael P. Stanley

(57) ABSTRACT

A miniature axisymmetric streamline tensile (MAST) specimen having improved axisymmetric surface profile design and surface stress concentration factor (SSCF) improvements, i.e., close to unity is described. The MAST specimen also has improved variable curvature transition fillets, miniaturized profile dimension and shoulder region features used in conjunction with the collet loading method. An axisymmetric, rather than flat, design is preferred since no stress gradients exist in the hoop direction, i.e., circumferential direction, of the specimen. The MAST specimen is designed to permit various loading options. The MAST specimen 10 may be used for testing any suitable material including, but not limited to, metals, plastics and ceramics.

14 Claims, 3 Drawing Sheets

MINIATURE AXISYMMETRIC STREAMLINE TENSILE (MAST) SPECIMEN

STATEMENT OF GOVERNMENT INTEREST

The invention described herein may be manufactured and used by or for the Government of the United States of America for Governmental purposes without the payment of any royalty thereon or therefor.

BACKGROUND OF THE INVENTION (1) Field of the Invention

This invention relates to a miniature axisymmetric streamline tensile (MAST) specimen that is to undergo tensile stress. This MAST specimen is axisymmetrical with transition regions (i.e., regions that transition from the constant diameter shoulder or grip regions near the end sections to the gauge section region) having variable curvature fillets and having a surface stress concentration factor (SSCF) close to unity.

(2) Description of the Prior Art

The Navy has a need to test piezoelectric ceramic materials in order to determine their performance in sonar transducers. The piezoelectric ceramic materials are typically grown as a single crystal which limits the size of the sample. These materials are very brittle and subject to cracking during use as a transducer. The Navy needs to know the useful life of these materials and the amount of stress that they can be subjected to while still being useful. It is also necessary to determine the electrical properties of the materials and how small flaws in the material affect these properties. No prior art test configuration properly gives this information for piezoelectric ceramics.

Tensile testing of ceramic materials using a standard tensile testing machine is not commonly performed because the tensile strength of ceramic materials is typically very sensitive to small cracks. These cracks are almost always present in normally sized specimens. In brittle materials, such as these ceramic materials, no energy is dissipated in plastic deformation ahead of the crack and the crack propagates easily. A bend test is more commonly used to determine the transverse rupture strength of a ceramic; however, this test does not give the true tensile strength of the material, and the ceramic is subject to failure at the points of load. Another problem is that properties determined using the bend test are not independent of the volume of material being tested.

The American Society for Testing and Materials (ASTM) is a large, not-for-profit, standards organization that provides a forum for producers, users, ultimate consumers, and those having a general interest to meet on common ground and write standards for materials, products, systems, and services. ASTM develops and publicizes voluntary consensus standards for materials, products, systems, and services. ASTM also publishes standard test methods, specifications, practices, guides, classifications, and terminology. ASTM's standards development activities encompass metals, paints, plastics, textiles, petroleum, construction, energy, the environment, consumer products, medical services and devices, computerized systems, electronics, and many other areas.

Several commonly used standardized tensile and compression specimen shapes can be found within the ASTM literature. Tension specimens are generally either flat or axisymmetric shaped. They are typically loaded for testing using wedge grips, collets, threaded ends or pinned ends. Typically, these existing specimen shapes are several inches or longer in length and include constant radius fillets that transition a grip region to a gauge section.

The use of constant curvature fillets, while reducing the complexity of specimen machining and costs, results in surface stress concentration factors (SSCF) ranging minimally from 1.10 to 1.20. A desired SSCF value is unity, 1.00. Furthermore, these specimens yield material strengths that are dependent upon specimen profiles.

With these specimens, the maximum stress may not occur within the gauge section where the applied stress field is assumed uniaxial. Rather, the maximum stress resides at a surface transition point where stress fields are neither uniaxial nor uniform, but rather biaxial and highly non-uniform. For materials that are brittle or lacking sufficient ductility, the surface transition points may become failure initiation regions, especially under dynamic fatigue loads. No suitable miniature axisymmetric standard tensile specimens were available that provide SSCFs close to unity.

The prior art discloses various testing specimens. One such prior art specimen is Van Winkle et al., U.S. Pat. No. 2,454,850, which is said to disclose a torsion specimen having a cylindrical gauge region.

Also known in the prior art is Scott et al., U.S. Pat. No. 4,606,230, which is said to disclose a tensile testing apparatus with a tensile specimen having a rectangular gauge section.

Also known are Pratt, U.S. Pat. No. 4,895,750, and Pratt, U.S. Pat. No. 5,078,843, which are said to disclose a carbon composite tensile test specimen for high temperature testing and a method of fabricating the same. The tensile test specimen has a central gauge section that appears to be curved and of constant dimension.

Also known is Hiyoshi, U.S. Publication No. 2002/0166386 A1, which is said to disclose a method and apparatus for measuring elongation in a contact-less manner capable of obtaining accurate measured value without attaching reference lines and capable of being automated wherein a test specimen has a straight, constant-width gauge section.

Also known is Oplinger et al., On the Streamline Specimen for Tension Testing of Composite Materials, Special Technical Testing Publication 864—American Society for Testing and Materials, pp. 541–542, Philadelphia, 1985, which is said to disclose the analogy between elastic stress fields and 2-D fluid flow through a reducer. Concerning the testing of fibrous composites, this publication teaches the use of a flat, streamlined specimen to reduce surface stress concentration factors to near unity. Wedge grips are used to hold the flat sample in the test apparatus.

Other devices and specimens are known for tensile and compression testing of various materials. These specimens, along with those above, have various shortcomings including having maximum stress not occurring within a gauge section, failure regions at surface transition points and surface stress concentration factors (SSCF) not at unity. The shortcomings of these specimens are addressed by the present invention.

SUMMARY OF THE INVENTION

A primary object of the present invention is to provide a miniature axisymmetric streamline tensile (MAST) specimen with a surface stress concentration factor (SSCF) close to unity, 1.0.

Another primary object of the present invention is to provide a MAST specimen with a surface profile consisting of variable curvature transition fillets and virtually stress concentration free surfaces compared to existing standardized specimens.

Another object of the present invention is to provide a MAST specimen with uniform axial stress fields within and adjacent to the gauge section unlike that of existing standardized specimens.

Another object of the present invention is to provide a MAST specimen with static and dynamic fatigue failure strengths which accurately reflect the material's true strength.

Another object of the present invention is to provide a MAST specimen which requires a smaller volume of material per specimen than existing standardized specimens.

Another object of the present invention is to provide a MAST specimen with lower material costs, machining costs and shipping and handling costs.

Accordingly, the present invention provides a MAST specimen having improved axisymmetric shaped design, variable curvature transition fillets, miniaturized profile dimension and shoulder region features used in conjunction with the collet loading method. An axisymmetric, rather than flat, design is preferred since no stress gradients exist in the hoop direction, i.e., circumferential direction, of the specimen. The MAST specimen of the present invention is designed to permit various loading options.

BRIEF DESCRIPTION OF THE DRAWING(S)

Reference is made to the accompanying drawings in which is shown an illustrative embodiment of the invention, from which its novel features and advantages will be apparent, wherein corresponding reference characters indicate corresponding parts throughout the several views of the drawings and wherein.

DESCRIPTION OF THE PREFERRED EMBODIMENT(S)

The present invention is a miniature axisymmetric streamline tensile (MAST) specimen 10 having improved axisymmetric surface profile design and surface stress concentration factor (SSCF) improvements, i.e., close to unity, 1.0. The MAST specimen 10 of the present invention also has improved variable curvature transition fillets 16, miniaturized profile dimension and shoulder 20 region features used in conjunction with the collet loading method. An axisymmetric, rather than flat, design is preferred since no stress gradients exist in the hoop direction, i.e., circumferential direction, of the specimen. The axisymmetric design requires shoulders 20 because wedge grips cannot be applied to a curved surface.

Figure 1:
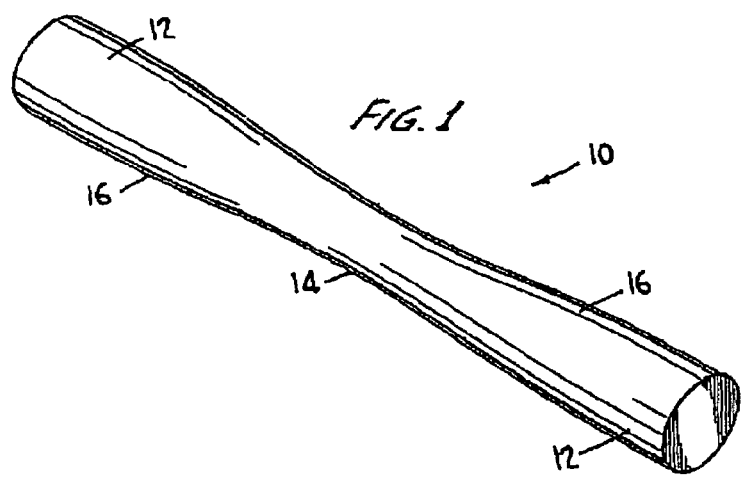
FIG. 1 illustrates a perspective view of a MAST specimen profile of the present invention.
Figure 2:
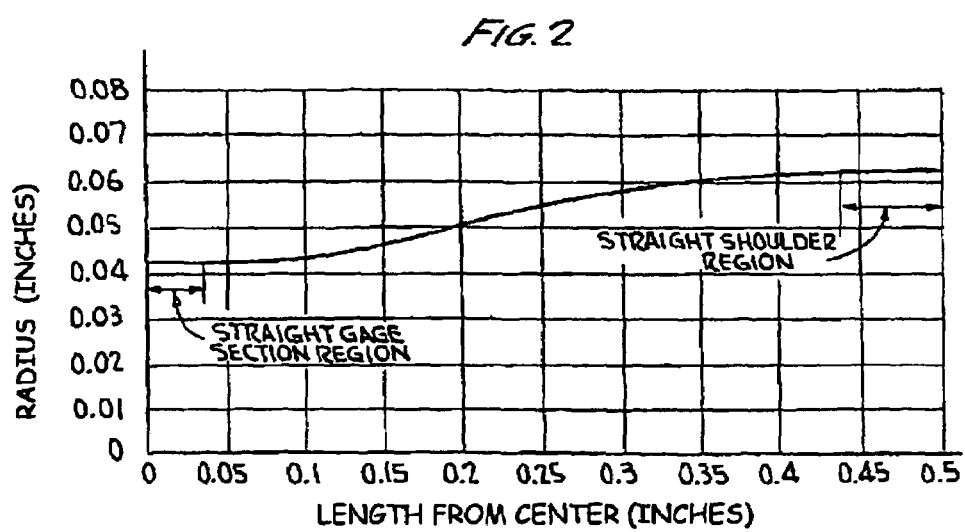
FIG. 2 illustrates a preferred variable curvature transition fillet of the MAST specimen of FIG. 1.

A preferred MAST specimen 10 profile of the present invention is shown in FIG. 1. The MAST specimen 10 has two axisymmetric end sections 12 and a substantially central axisymmetric gauge section 14. A variable curvature transition fillet 16 provides a transition between each end section 12 and the substantially central gauge section 14. FIG. 2 shows a preferred first quadrant profile of a MAST specimen 10 showing a preferred variable curvature transition fillet 16. This transition fillet 16 can be calculated as a traction-free boundary with an offset distance. The offset distance provides improved handling characteristics. The offset is also used to create the same cross sectional area as other samples for comparison.

The MAST specimen 10 of the present invention is designed to permit various loading options. For example, the MAST specimen 10 may be loaded using collets, threaded ends, etc. However, the collet method requires that the MAST specimen 10 be machined to include oversized load bearing shoulders 20 on each end section 12 to eliminate the possibility of a bearing stress-induced fracture within this load transfer region prior to failing the gauge section 14.

Figure 3:
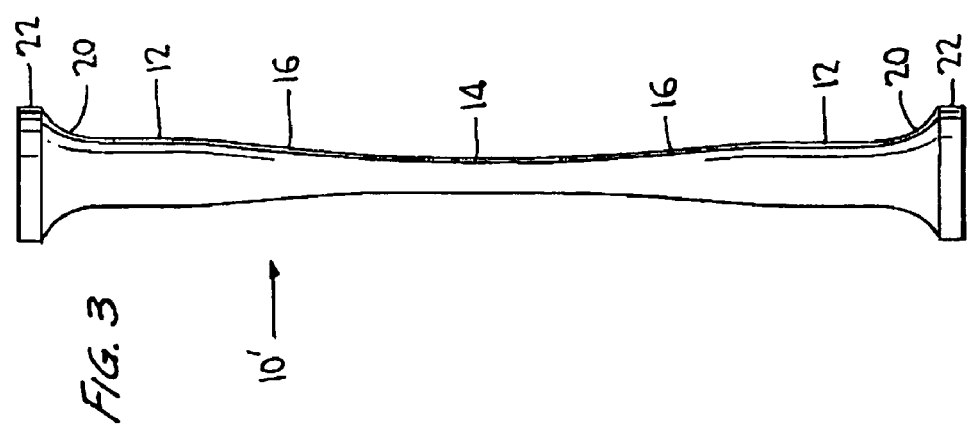
FIG. 3 illustrates a side view of a collet version of the MAST specimen of FIG. 1.

A collet version of the MAST specimen 10 is shown in FIG. 3. A collet 22 is located near the free end of each end section 12. A shoulder 20 provides a transition between each collet 22 and each respective end section 12. The collet version 10' of the MAST specimen 10 must be sized to avoid bearing stress failures in the shoulder 20. For example, a collet-loaded MAST specimen 10' having a maximum SSCF of 1.01 and a length of 1.0 inch will preferably have a resulting gauge section 14 diameter of 0.042 inch. Because this diameter is relatively small, extreme care must be used in installing the specimen within the test machine. Otherwise, MAST specimen breakage may occur during test set-up. However, any suitable length and gauge section 14 diameter may be used for the MAST specimen 10, 10'.

Figure 4:
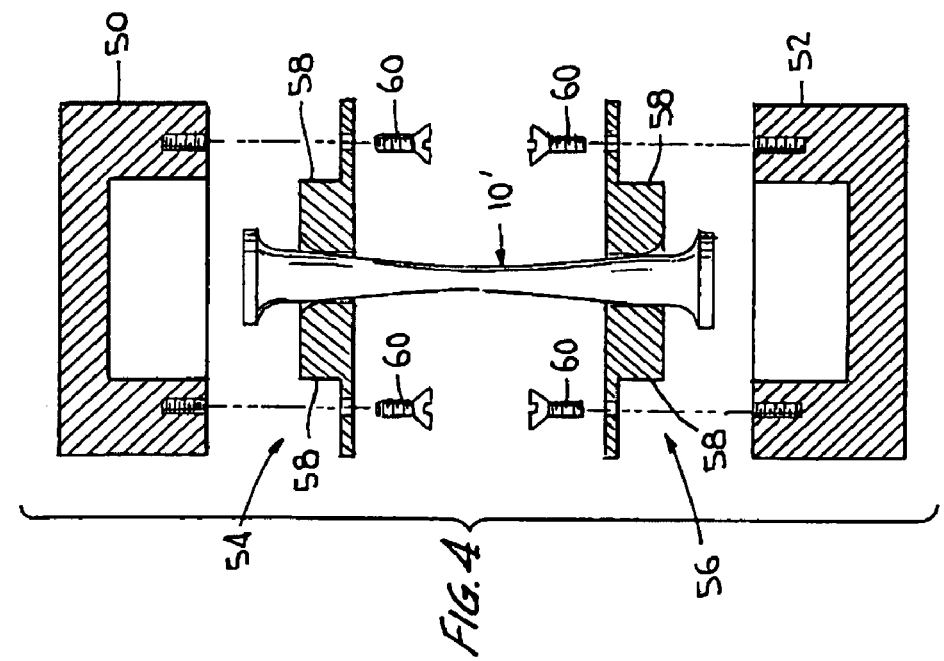
FIG. 4 illustrates a side view of a collet MAST specimen and hardware required for collet loading of a collet MAST specimen of FIG. 1.

FIG. 4 shows the hardware required for collet loading. This test block hardware preferably includes an upper grip holder 50, a lower grip holder 52, an upper cover plate set 54 and a lower cover plate set 56. Each cover plate set 54, 56 preferably has annealed copper collets 58 and screws 60 for fastening each cover plate set 54, 56 to the respective grip holder 50, 52. This collet loaded embodiment promotes alignment of the specimen with the direction of the load. The shoulders of the specimen act to center the specimen within collets 58.

Figure 5:
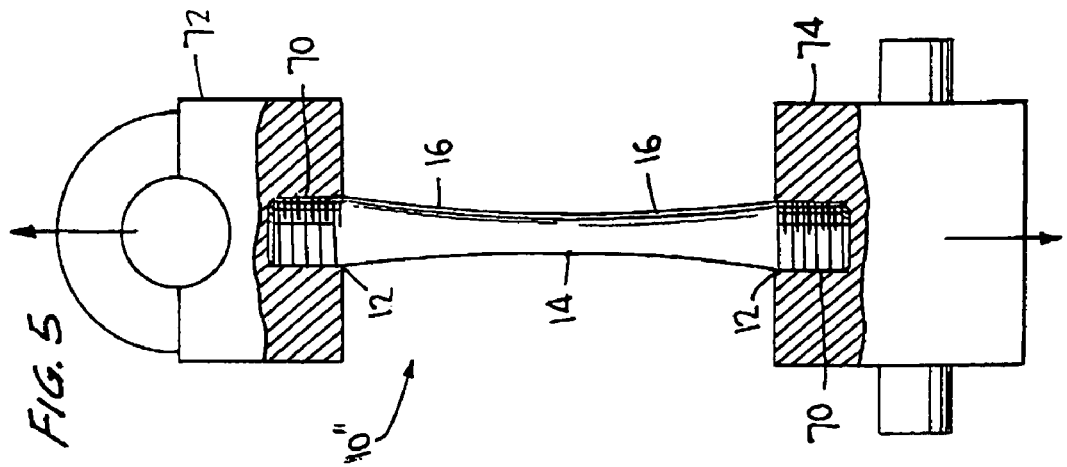
FIG. 5 illustrates a side section view of threaded end loading of a threaded MAST specimen of FIG. 1.

Another preferred embodiment of the MAST specimen 10 is the threaded MAST specimen 10", shown in FIG. 5. In this embodiment, threaded regions 70 are formed, cut into or attached to each end of the specimen 10". The specimen 10" can then be mounted in test blocks 72 and 74 prior to testing. This embodiment affords a greater gauge section 14 diameter since threaded region 70 stress can be distributed over a larger surface area than found in the collet method.

In either embodiment, universal joints are recommended within the specimen-to-test machine load train to eliminate any misalignment effects on the specimen that could otherwise result in specimen breakage. For example, a threaded end MAST specimen 10" having a maximum SSCF of 1.01 and a length of 1.0 inch will preferably have a resulting gauge section 14 diameter of approximately 0.080 inch, which is nearly double the gauge section 14 diameter of a preferred embodiment of a collet MAST specimen 10'. However, any suitable length and gauge section diameter may be used for the MAST specimen 10, 10".

An exemplary use of the MAST specimen 10 of the present invention is in the area of new generation piezoelectric materials such as Single Crystal PMN, i.e., Single Crystal Lead Magnesium Niobate. During testing, new generation piezoelectric materials, such as Single Crystal PMN, cannot be grown to the sizes required by most standardized tensile test specifications. Today, manufacturing methods for this material are limited to a maximum nominal size of only one inch. Therefore, to obtain accurate mechanical properties for the Single Crystal PMN that are ideally independent of both specimen size and profile, the MAST specimen of the present invention was developed with surface stress concentration factors (SSCF) approaching 1.0. This could only be accomplished by the MAST specimen 10 containing variable curvature fillets 16 in transition regions.

Primary advantages of the MAST specimen 10 of the present invention include, but are not limited to, surface stress concentration factors (SSCF) close to unity, a surface profile consisting of variable curvature transition fillets 16, virtually stress concentration free surfaces compared to existing standardized specimens, uniform axial stress fields within and adjacent to the gauge section 14 unlike that of existing standardized specimens and static and dynamic fatigue failure strengths which accurately reflect a material's true strength. The MAST specimen 10 also requires a smaller volume of material per specimen than existing standardized specimens. The MAST specimen 10 may be used for testing any suitable material including, but not limited to, metals, plastics and ceramics.

While the impetus of developing the MAST specimen 10 was to obtain a miniature specimen shape having substantial improvements over existing specimen designs found in the prior art, the MAST specimen 10 can be scaled for specimens regardless of size and loading methods. Additionally, the SSCF improvements also make the MAST specimen 10 a highly suitable specimen shape for compression testing of materials. However, from the compression perspective, the specimen diameters must be increased to avoid buckling failures prior to gauge section 14 compression failures.

In order to prepare the MAST specimen 10, a single crystal sample of the material, such as a piezoelectric material, used for the test is grown. This crystal sample is then machined to the disclosed profile utilizing numerically controlled manufacturing. Preferably, the specimen 10 is cut down from the single crystal axially. This avoids radial scribing which can create surface stress concentrators. As an alternative, the specimen 10 can be made, i.e., machined, using a numerically controlled lathe which will leave radial scribing such that the surface of the specimen has a surface stress concentration factor near unity. The radial scribing on the surface of the specimen can then be polished away. In either case, it is best that the numerically controlled machine follow the streamline equation with sufficient accuracy to avoid stress concentrators. This can be done by using point to point machining on a large set of points or by using a machine capable of following an equation precisely.

Figure 6:
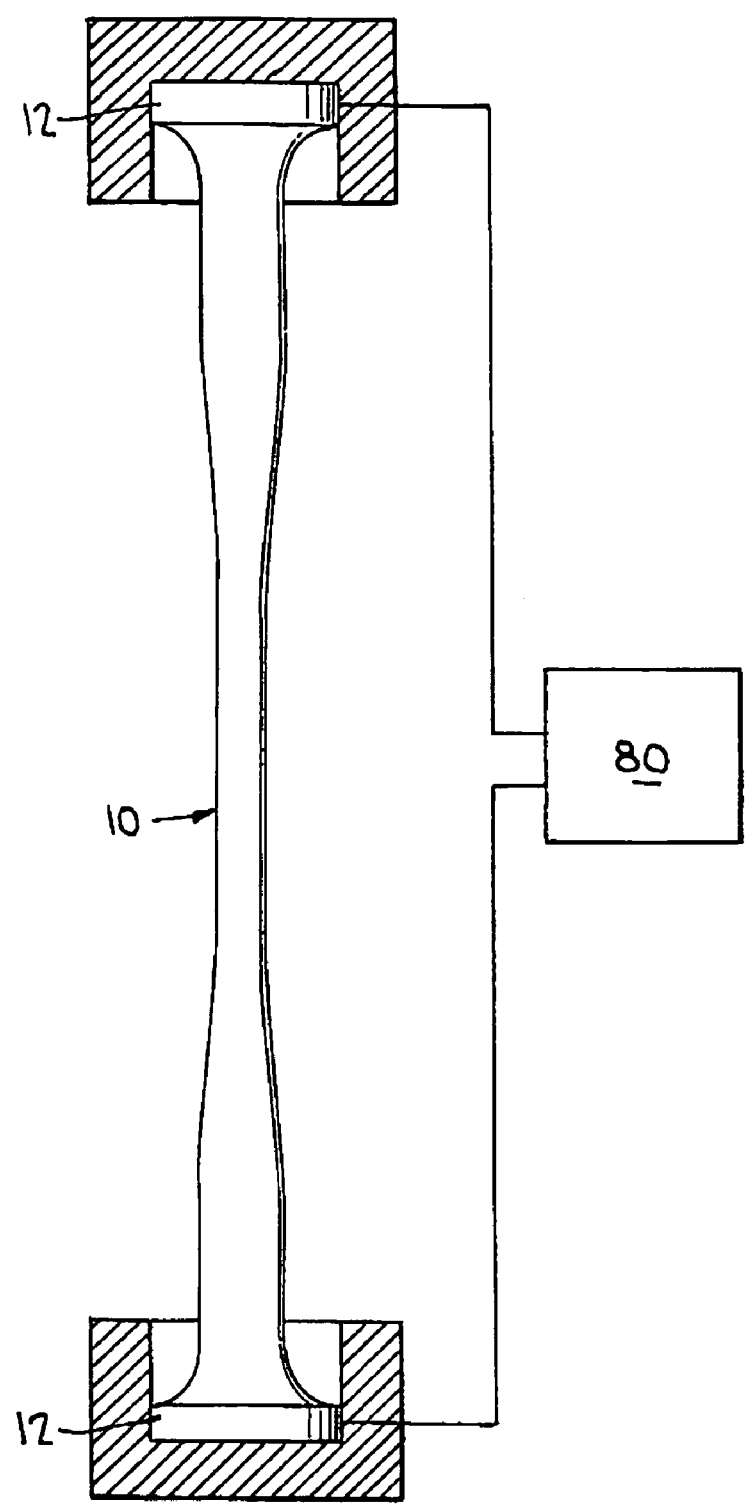
FIG. 6 illustrates a diagram of a test apparatus for piezoelectric specimens.

When a specimen is made from a piezoelectric material, it is desirable to monitor the specimen's electrical properties while it is being tested. FIG. 6 shows a test setup for this purpose. Electrical equipment 80 is electrically joined to each end section 12 of the specimen 10 such as by test blocks. The electrical equipment 80 should be capable of recording the voltage, current, impedance and resistance of the specimen 10 while it is being tested.

The specimen 10 can be tested using a standard mechanical tensile test where the ends of the specimen are drawn apart from each other until the specimen breaks or the specimen can be loaded by providing an electrical difference voltage at each end of the specimen 10 causing it to contract. This can be performed by electrical equipment 80 attached to the test blocks, which may apply an electrical current to the specimen cyclically to cause cyclical contractions. In either test, the specimen 10 can be cyclically loaded.

During testing, the specimen 10 may be subjected to axial forces, preferably performed mechanically, until failure. In a preferred embodiment, subjecting the specimens to axial forces until failure comprises causing contraction of the specimen by providing an electrical current to the specimen. The elongation of the specimen, the axial forces on the specimen, and the electrical properties of the specimen may be measured during testing. After the specimen destructively fails, it is microscopically examined to find the flaw causing the failure. Other properties measured from the specimen are stress, strain, cycle life, power output and acceptable flaw size.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

What is claimed is:

1. A tensile specimen comprising:
   an axisymmetric first end section;
   an axisymmetric second end section;
   an axisymmetric gauge section positioned centrally between said axisymmetric first end section and said axisymmetric second end section, wherein said axisymmetric first end section adjoins said axisymmetric gauge section by a first variable curvature transition fillet, and wherein said axisymmetric second end section adjoins said axisymmetric gauge section by a second variable curvature transition fillet, wherein said tensile specimen has a surface stress concentration factor close to unity (1.0);
   a first threaded portion positioned substantially near a free end of said axisymmetric first end section; and
   a second threaded portion positioned substantially near a free end of said axisymmetric second end section;
   wherein a maximum said surface stress concentration factor is 1.01, a length of said MAST specimen is 1.0 inch and a diameter of said axisymmetric gauge section is 0.080 inch.

2. A tensile specimen comprising:
   an axisymmetric first end section;
   an axisymmetric second end section; and
   an axisymmetric gauge section positioned centrally between said axisymmetric first end section and said axisymmetric second end section, wherein said axisymmetric first end section adjoins said axisymmetric gauge section by a first variable curvature transition fillet, and wherein said axisymmetric second end section adjoins said axisymmetric gauge section by a second variable curvature transition fillet, wherein said tensile specimen has a surface stress concentration factor close to unity (1.0);
   a first collet positioned substantially near a free end of said axisymmetric first end section, wherein said first collet adjoins said free end of said axisymmetric first end section by a first shoulder; and
   a second collet positioned substantially near a free end of said axisymmetric second end section, wherein said second collet adjoins said free end of said axisymmetric second end section by a second shoulder;

wherein a maximum said surface stress concentration factor is 1.01, a length of said MAST specimen is 1.0 inch and a diameter of said axisymmetric gauge section is 0.042 inch.

3. The tensile specimen according to claim 2, having a first load transfer region defined by said first shoulder and said axisymmetric first end section, and a second load transfer region defined by said second shoulder and said axisymmetric second end section wherein said first shoulder and said second shoulder are oversized load bearing shoulders which eliminate the possibility of a bearing stress-induced fracture within the first load transfer region and the second load transfer region prior to failing said axisymmetric gauge section.

4. The tensile specimen according to claim 2, wherein uniform axial stress fields exist within and adjacent to said axisymmetric gauge section.

5. A tensile specimen test setup comprising:
a tensile specimen having:
an axisymmetric first end section;
an axisymmetric second end section; and
an axisymmetric gauge section positioned centrally between said axisymmetric first end section and said axisymmetric second end section, wherein said axisymmetric first end section adjoins said axisymmetric gauge section by a first variable curvature transition fillet, and wherein said axisymmetric second end section adjoins said axisymmetric gauge section by a second variable curvature transition fillet, wherein said tensile specimen has a surface stress concentration factor close to unity (1.0);
a first test block attached to said axisymmetric first end section of said tensile specimen;
a second test block attached to said axisymmetric second end section of said tensile specimen; and
an electrical apparatus electrically joined to said first test block and said second test block, wherein said electrical apparatus records voltage, current, impedance and resistance of said tensile specimen while said tensile specimen is tested.

6. The tensile specimen test setup according to claim 5, wherein said tensile specimen further comprises:
a first collet located substantially near a free end of said axisymmetric first end section, wherein said first collet adjoins said free end of said axisymmetric first end section by a first shoulder; and
a second collet located substantially near a free end of said axisymmetric second end section, wherein said second collet adjoins said free end of said axisymmetric second end section by a second shoulder, wherein said first test block is adapted to receive said collet of said axisymmetric first end section and said second test block is adapted to receive said collet of said axisymmetric second end section.

7. The tensile specimen test setup according to claim 5, further comprising:
a first threaded portion positioned substantially near a free end of said axisymmetric first end section; and
a second threaded portion positioned substantially near a free end of said axisymmetric second end section;
wherein said first test block is adapted to receive said threaded portion of said axisymmetric first end section and said second test block is adapted to receive said threaded portion of said axisymmetric second end section.

8. A method of testing a piezoelectric material comprising:
preparing a sample from a piezoelectric material;
mounting said sample to a mounting apparatus;
joining electrical measurement apparatus to said sample by said mounting apparatus;
subjecting said sample to axial forces until failure;
measuring elongation of said sample during said step of subjecting;
measuring axial forces on said sample during said step of subjecting;
measuring electrical properties of said sample during said step of subjecting; and
examining said sample after failure.

9. The method of claim 8, wherein subjecting said sample to axial forces until failure comprises causing contraction of said sample by providing an electrical current to said sample.

10. The method of claim 9, wherein said electrical current is provided to said sample cyclically to cause cyclical contractions.

11. The method of claim 8, wherein subjecting said sample to axial forces is performed mechanically.

12. The method of claim 8, wherein preparing said sample from said piezoelectric material comprises:
growing a crystal of said piezoelectric material; and
machining a cylindrical tensile test specimen from said crystal.

13. The method of claim 12, wherein machining said tensile test specimen comprises:
using a numerically controlled lathe to radially scribe said tensile test specimen such that a surface of said tensile test specimen has a surface stress concentration factor near unity; and
polishing said surface of said tensile test specimen.

14. The method of claim 12, wherein machining said tensile test specimen comprises using a numerically controlled machine to axially scribe said tensile test specimen such that a surface of said tensile test specimen has a surface stress concentration factor near unity.

* * * * *